(12) United States Patent
Butler et al.

(10) Patent No.: US 7,371,911 B2
(45) Date of Patent: May 13, 2008

(54) CRITICAL PHASE ALKYLATION AND TRANSALKYLATION PROCESS IN THE PRESENCE OF A BETA ZEOLITE

(75) Inventors: James R. Butler, Houston, TX (US); Kevin P. Kelly, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 520 days.

(21) Appl. No.: 11/066,951

(22) Filed: Feb. 25, 2005

(65) Prior Publication Data

US 2006/0194994 A1 Aug. 31, 2006

(51) Int. Cl.
C07C 2/66 (2006.01)

(52) U.S. Cl. ...................... 585/467; 585/475

(58) Field of Classification Search ......... 585/467, 585/475
See application file for complete search history.

(56) References Cited

U.S. PATENT DOCUMENTS

| | | | |
|---|---|---|---|
| 4,891,458 A * | 1/1990 | Innes et al. | 585/323 |
| 5,145,817 A | 9/1992 | Sherrod | |
| 5,907,073 A | 5/1999 | Ghosh | |
| 6,627,781 B1 | 9/2003 | Briot et al. | |
| 7,268,264 B2 | 9/2007 | Butler et al. | |
| 2004/0138511 A1 | 7/2004 | Butler | |

* cited by examiner

Primary Examiner—Thuan Dinh Dang
(74) Attorney, Agent, or Firm—Shirley A. Kopecky; William D. Jackson (57) ABSTRACT

A process for the production of ethylbenzene by the ethylation of benzene in the critical phase in a reaction zone containing a molecular sieve aromatic alkylation catalyst comprising cerium-promoted zeolite beta. A polyethylbenzene is supplied into the reaction zone and into contact with the cerium-promoted zeolite beta having a silica/alumina mole ratio within the range of 20-500. The reaction zone is operated at temperature and pressure conditions in which benzene is in the supercritical phase to cause ethylation of the benzene and the transalkylation of polyethylbenzene and benzene in the presence of the zeolite beta catalyst. An alkylation product is produced containing ethylbenzene as a primary product with the attendant production of heavier alkylated byproducts of no more than 60 wt. % of the ethylbenzene. The alkylation reaction zone is operated under conditions providing a composite byproduct yield of propyl benzene and butyl benzene relative to ethylbenzene, which is no more than one half of the corresponding yield byproduct for zeolite beta promoted with lanthanum. The production of ethylbenzene in the critical phase alkylation reaction zone is attended by recycle of a polyalkylated aromatic component of the reaction product back to the reaction zone.

20 Claims, 4 Drawing Sheets

CRITICAL PHASE ALKYLATION AND TRANSALKYLATION PROCESS IN THE PRESENCE OF A BETA ZEOLITE

FIELD OF THE INVENTION

This invention relates to the production of ethylbenzene and more particularly to the ethylation of benzene and the transalkylation of polyethylbenzene and benzene over a cerium-promoted beta alkylation catalyst under conditions in which the benzene is in the supercritical phase.

BACKGROUND OF THE INVENTION

The alkylation of benzene with ethylene over a molecular sieve catalyst is a well known procedure for the production of ethylbenzene. Typically, the alkylation reaction is carried out in a multistage reactor involving the interstage injection of ethylene and benzene to produce an output from the reactor that involves a mixture of monoalkyl and polyalkylbenzenes. The principal monoalkylbenzene is, of course, the desired ethylbenzene product. Heavier byproducts, which are generally undesirable, include polyalkylbenzenes such as diethylbenzene, triethylbenzene, xylenes and diphenyl products such as 1,1 diphenyl ethane.

In many cases, it is desirable to operate the alkylation reactor in conjunction with the operation of a transalkylation reactor in order to produce additional ethylbenzene through the transalkylation reaction of polyethylbenzene with benzene. The alkylation reactor can be connected to the transalkylation reactor in a flow scheme involving one or more intermediate separation stages for the recovery of ethylene, ethylbenzene, and polyethylbenzene.

Transalkylation may also occur in the initial alkylation reactor. In this respect, the injection of ethylene and benzene between stages in the alkylation reactor not only results in additional ethylbenzene production, but also promotes transalkylation within the alkylation reactor in which benzene and diethylbenzene react through a disproportionation reaction to produce ethylbenzene.

Various phase conditions may be employed in the alkylation and transalkylation reactors. Typically, the transalkylation reactor will be operated under liquid phase conditions, i.e., conditions in which the benzene and polyethylbenzene are in the liquid phase, and the alkylation reactor is operated under gas phase conditions, i.e., pressure and temperature conditions in which the benzene is in the gas phase. However, liquid phase conditions can be used where it is desired to minimize the yield of undesirable byproducts from the alkylation reactor.

SUMMARY OF THE INVENTION

In accordance with the present invention, there is provided a process for the production of ethylbenzene by the ethylation of benzene in the critical phase in a reaction zone containing a molecular sieve aromatic alkylation catalyst comprising cerium-promoted zeolite beta. In addition, a polyethylbenzene is supplied into the reaction zone and into contact with the cerium-promoted zeolite beta. Preferably, the zeolite beta has a silica/alumina mole ratio within the range of 20-500 and more, preferably within the range of 50-150. Ethylene is supplied to the alkylation reaction zone in an amount to provide a benzene/ethylene mole ratio of 1-15. The reaction zone is operated at temperature and pressure conditions in which benzene is in the supercritical phase to cause ethylation of the benzene and the transalkylation of polyethylbenzene and benzene in the presence of the zeolite beta catalyst. An alkylation product is produced containing ethylbenzene as a primary product with the attendant production of heavier alkylated byproducts. Such byproducts normally will be no more than 60 wt. % of the ethylbenzene. The alkylation product is recovered from the reaction zone for further use or processing. Preferably, the alkylation reaction zone is operated under temperature and pressure conditions providing a composite byproduct yield of propyl benzene and butyl benzene relative to ethylbenzene, which is no more than one half of the corresponding yield byproduct for zeolite beta promoted with lanthanum.

The production of ethylbenzene in the critical phase alkylation reaction zone is attended by recycle of a polyalkylated aromatic component of the reaction product back to the reaction zone. The alkylation reaction zone is operated at temperature and pressure conditions at which benzene is in the super critical phase to cause ethylation of the benzene in the presence of the cerium-promoted zeolite beta and to produce an alkylation product comprising a mixture of benzene, ethylbenzene, and polyalkylated aromatics, including diethylbenzene. The alkylation product is recovered from the alkylation reaction zone and supplied to a separation and recovery zone. In the recovery zone, ethylbenzene is separated and recovered from the product. A polyalkylated component including diethylbenzene is also separated from the product. At least a portion of the polyalkylated aromatic component, including diethylbenzene, is recycled to the critical phase reactor zone. In one embodiment of the invention, another portion of the polyalkylated product is supplied to a separate transalkylation reaction zone containing a molecular sieve transalkylation catalyst. Benzene is also supplied to the transalkylation reaction zone, and the transalkylation reaction zone is operated under temperature and pressure conditions to cause disproportionation of the polyalkylated aromatic fraction to produce a disproportionation product having a reduced diethylbenzene content and an enhanced ethylbenzene content. Preferably, the transalkylation reaction zone contains a zeolite Y catalyst and is operated under conditions to maintain the polyalkylated aromatic component in the liquid phase. Preferably, the cerium-promoted zeolite beta has a cerium/aluminum ratio within the range of 0.25-5.0, more preferably 0.5-1.5.

DETAILED DESCRIPTION OF THE INVENTION

The present invention involves the critical phase alkylation of benzene over a cerium-promoted zeolite beta alkylation catalyst coupled with transalkylation of benzene and polyethylbenzene under conditions to control and desirably minimize the yield of byproducts in the reaction zone. The feedstock supplied to the alkylation reaction zone comprises benzene and ethylene. Typically, the benzene and ethylene streams will be combined to provide a benzene-ethylene mixture into the reaction zone. The benzene stream, which is mixed with the ethylene either before or after introduction into the reaction zone, should be a relatively pure stream containing only very small amounts of contaminants. The benzene stream should contain at least 90 wt. % benzene. Preferably, the benzene stream will be at least 95 wt. % benzene, and more preferably at least 98 wt. % benzene, with only trace amounts of such materials as toluene, ethylbenzene, and $C_7$ aliphatic compounds that cannot readily be separated from benzene. The alkylation/transalkylation reaction zone is operated under supercritical conditions, that is, pressure and temperature conditions which are above the critical pressure and critical temperature of benzene. Specifically, the temperature in the alkylation zone is at or above 300° C., and the pressure is at or above 715 psia. Preferably, the temperature in the alkylation reactor will be maintained at an average value within the range of 275-350° C. and a pressure within the range of 750-850 psia. If desired higher alkylation temperatures can be employed since the cerium-promoted zeolite beta retains its structural integrity at temperatures of about 530-540° C. Zeolite beta which has not been promoted with cerium tends to lose its structural integrity as the temperature reaches 500° C. The critical phase alkylation reaction is exothermic with a positive temperature gradient from the inlet to the outlet of the reactor, providing a temperature increment increase of about 40°±10° C.

The operation of the alkylation reaction zone in the supercritical region enables the alkylation zone to be operated under conditions in which the benzene-ethylene mole ratio can be maintained at relatively low levels, usually somewhat lower than the benzene-ethylene mole ratio encountered when the alkylation reaction zone is operated under liquid phase conditions. In most cases, the benzene-ethylene mole ratio will be within the range of 1-15. Preferably, the benzene mole ratio will be maintained during at least part of a cycle of operation at a level within the lower end of this range, specifically, at a benzene-ethylene mole ratio of less than 10. A benzene-ethylene mole ratio within the range of 2-8, and preferably 2-5, may be employed. Thus, operation in the supercritical phase offers advantages similar to those achieved by gas phase alkylation, in which the benzene-ethylene ratio can be kept low, but without the problems associated with byproduct formation, specifically xylene formation, often encountered in gas-phase alkylation. At the same time, operation in the supercritical phase offers the advantages accruing to liquid phase alkylation in which the byproduct yield is controlled to low levels. The pressures required for operation in the supercritical phase are not substantially greater than those required in liquid phase alkylation, and the benzene in the supercritical phase functions as a solvent to keep the zeolite beta catalyst clean and to retard coking leading to deactivation of the catalyst.

The cerium-promoted beta enables super critical phase alkylation to be carried out with byproducts that are substantially less than the corresponding byproducts produced with super critical phase alkylation employing lanthanum-promoted zeolite beta of similar or greater metal content. Thus, the alkylation reaction zone can be operated at supercritical phase temperature and pressure conditions to provide a composite byproduct yield of propylbenzene and butylbenzene which is less than the corresponding composite byproduct yield of propylbenzene and butylbenzene for a corresponding zeolite beta catalyst promoted with lanthanum at a lanthanum/beta atomic ratio at least as great as the cerium/aluminum atomic ratio of the cerium-promoted zeolite beta. Preferably, the alkylation reaction zone is operated at temperature and pressure conditions to provide a composite product yield of propylbenzene and butylbenzene which is no more than one-half of the corresponding composite byproduct yield of propylbenzene and butylbenzene produced with the lanthanum-promoted zeolite beta.

Figure 1:
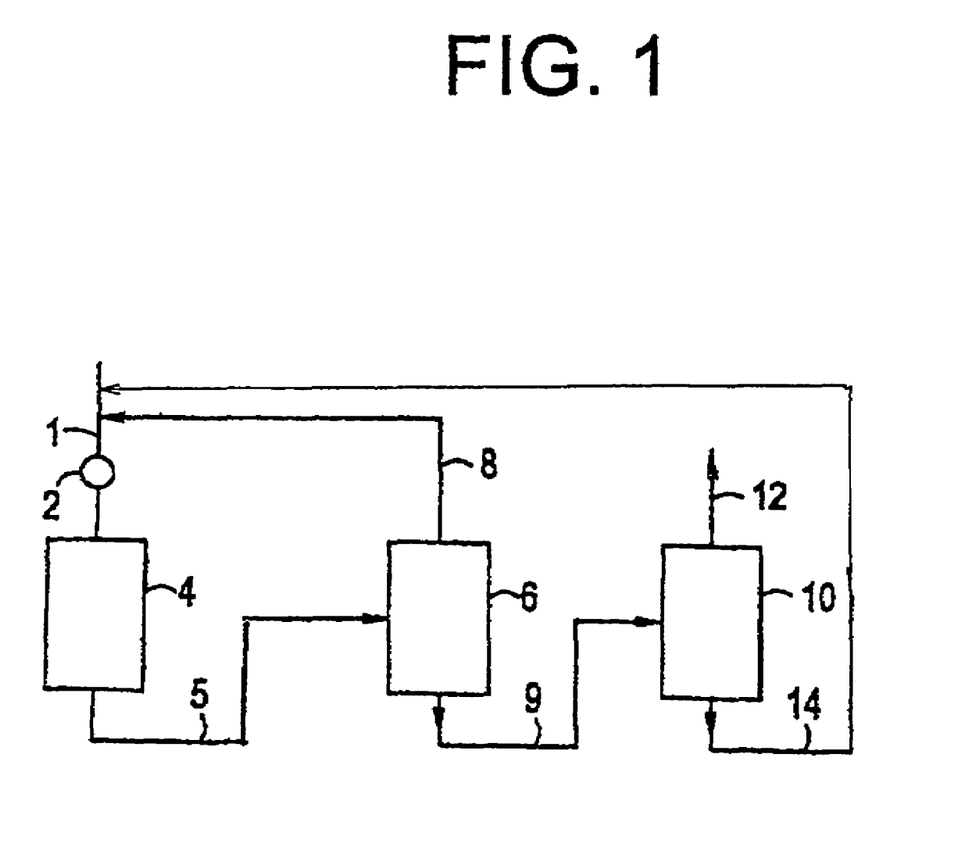
FIG. 1 is an idealized schematic block diagram of an alkylation/transalkylation process embodying the present invention.

Turning now to FIG. 1, there is illustrated a schematic block diagram of an alkylation/transalkylation process employing the present invention. As shown in FIG. 1, a product stream comprising a mixture of ethylene and benzene in a mole ratio of benzene to ethylene of about 1 to 15 is supplied via line 1 through a heat exchanger 2 to an alkylation/transalkylation reaction zone 4. Reaction zone 4 preferably comprises one or more multi-stage reactors having a plurality of series-connected catalyst beds containing a cerium-promoted zeolite beta alkylation catalyst as described herein. The alkylation zone 4 is operated at temperature and pressure conditions to maintain the alkylation reaction in the supercritical phase, i.e. the benzene is in the supercritical state, and at a feed rate to provide a space velocity enhancing ethylbenzene production while retarding byproducts production. Preferably, the space velocity of the benzene feed stream will be within the range of 10-150 hr.$^{-1}$ LHSV per bed.

The output from the alkylation reactor 4 is supplied via line 5 to an intermediate benzene separation zone 6 that may take the form of one or more distillation columns. Benzene is recovered through line 8 and recycled through line 1 to the alkylation reactor. The bottoms fraction from the benzene separation zone 6, which includes ethylbenzene and polyalkylated benzenes including polyethylbenzene, is supplied via line 9 to an ethylbenzene separation zone 10. The ethylbenzene separation zone may likewise comprise one or more sequentially connected distillation columns. The ethylbenzene is recovered through line 12 and applied for any suitable purpose, such as in the production of vinyl benzene. The bottoms fraction from the ethylbenzene separation zone 10, which comprises polyethylbenzene, principally diethylbenzene, is supplied via line 14 for recycle to reactor 4 where it is employed in a transalkylation reaction with benzene supplied to the reactor.

Upon recycle of the polyethylbenzene to the reactor, the following concurrent reactions occur over the cerium-promoted zeolite beta catalyst. Ethylene reacts with benzene to produce ethylbenzene, usually accompanied by the production of smaller amounts of diethyl benzene and even smaller amounts of triethylbenzene. In addition, benzene reacts in a transalkylation reaction with diethyl benzene, and possibly with smaller amounts of triethylbenzene, in order to produce ethylbenzene. A side reaction can involve the reaction of ethylene and benzene to produce 1,1-diphenylethane. The conditions are controlled in the reactor so that the reactor temperature is above the critical temperature and pressure of benzene so that the benzene is in the supercritical phase. The ethylbenzene may be in either the liquid or supercritical phase, but usually will be in the liquid phase. The heavier aromatics such as polyethylbenzene will normally be in the liquid phase, that is, the reactor temperature is below the critical temperature for the diethylbenzene and other polyethylbenzenes. Under severe reactor conditions, the temperature may be sufficient to maintain the ethylbenzene in the critical phase as well as maintaining the benzene in the critical phase. The heavier polyethylbenzenes or polynuclear compounds such as 1,1-diphenylethane will, in any case, normally be in liquid phase.

Figure 2:
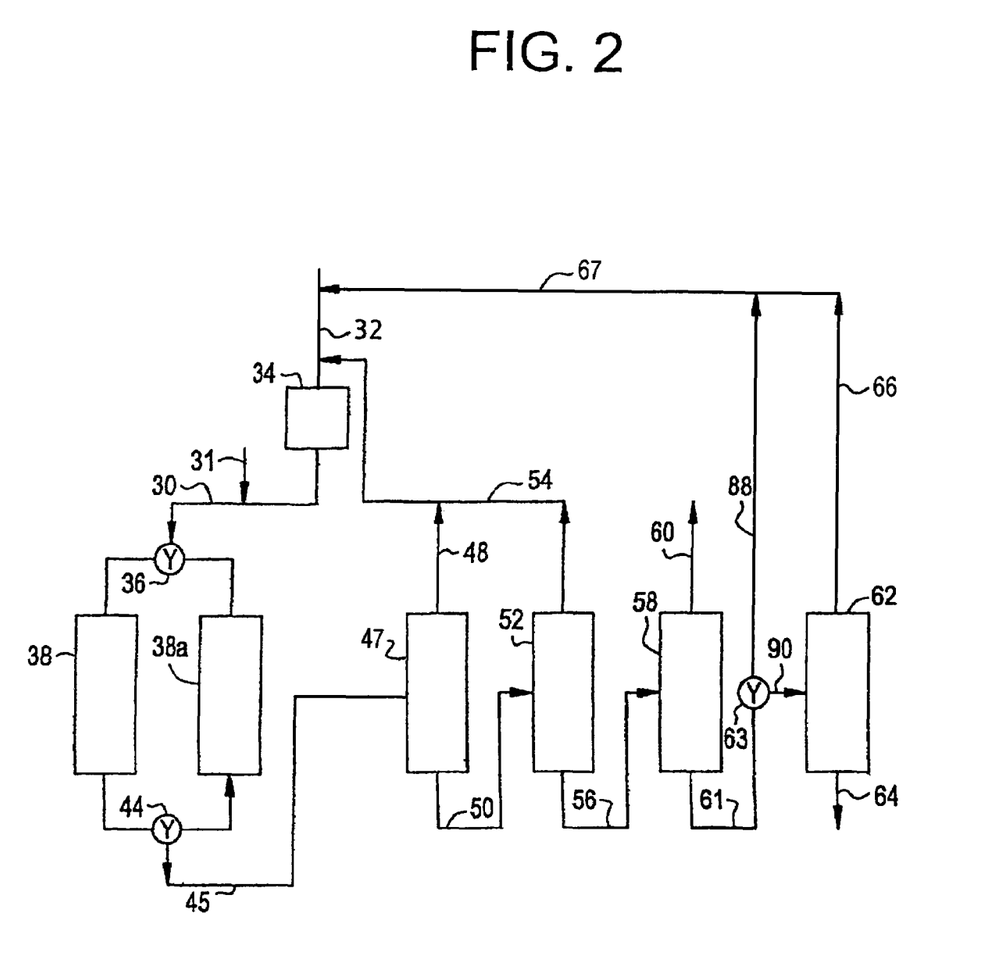
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the critical phase alkylation and transalkylation process. As shown in FIG. 2, an input feed stream is supplied by fresh ethylene through line 31 and fresh benzene through line 32. As noted previously, the fresh benzene stream supplied via line 32 preferably is of high purity containing at least 98 wt. %, preferably about 99 wt. % benzene with no more than 1 wt. % other components. Preferably, the fresh benzene stream will contain about 99.5 wt. % benzene, less than 0.5% ethylbenzene, with only trace amounts of non-aromatics and toluene. Line 32 is provided with a preheater 34 to heat the benzene stream consisting of fresh and recycled benzene to the desired temperature for the supercritical alkylation reaction. The feed stream is supplied through a two-way, three-position valve 36 and inlet line 30 to the top of one or both parallel critical phase alkylation/transalkylation reactors 38 and 38a comprising a plurality of series connected catalyst beds each of which contains the desired molecular sieve alkylation catalyst. The reactors are operated at an average temperature, preferably within the range of 275-350° C. inlet temperature and at pressure conditions of about 715 to 800 psia, to maintain the benzene in the critical phase. As mentioned previously, because of the high temperature structural integrity of cerium-promoted zeolite beta, the alkylation reaction zone can be operated at temperatures of up to about 500° C. and even beyond that to temperatures of about 540° C.

In normal operation of the system depicted in FIG. 2, both reaction zones 38 and 38a may, during most of a cycle of operation, be operated in a parallel mode of operation in which they are both in service at the same time. In this case, valve 36 is configured so that the input stream in line 30 is roughly split in two to provide flow to both reactors in approximately equal amounts. Periodically, one reactor can be taken off-stream for regeneration of the catalyst. Valve 36 is then configured so that all of the feed stream from line 30 can be supplied to reactor 38 while the catalyst beds in reactor 38a are regenerated and vise versa. The regeneration procedure will normally take place over a relatively short period of time relative to the operation of the reactor in parallel alkylation mode. The regeneration procedure preferably is carried out at temperatures substantially in excess of those normally employed in the regeneration of zeolite beta-type catalysts. When regeneration of the catalyst beds in reactor 38a is completed, this catalyst can then be returned on-stream and at an appropriate point, the reactor 38 can be taken off-stream for regeneration. This mode of operation involves operation of the individual reactors at relatively lower space velocities for prolonged periods of time with periodic relatively short periods of operation at enhanced, relatively higher space velocities when one reactor is taken off-stream. By way of example, during normal operation of the system with both reactors 38 and 38a on-stream, the benzene in the feed stream is supplied to each reactor to provide a space velocity of about 25-45 hr.$^{-1}$ LHSV. When reactor 38a is taken off-stream and the feed rate continues unabated, the space velocity for reactor 38 will approximately double to 50-90 hr.$^{-1}$ LHSV. When the regeneration of reactor 38a is completed, it is placed back on-stream and again the feed stream rate space velocity for each reactor will decrease to 25-45 hr.$^{-1}$ until such point as reactor 38 is taken off-stream, in which case the flow rate to reactor 38a will, of course, increase, resulting again in a transient space velocity in reactor 38 of about 50-90 hr.$^{-1}$ LHSV.

Figure 3:
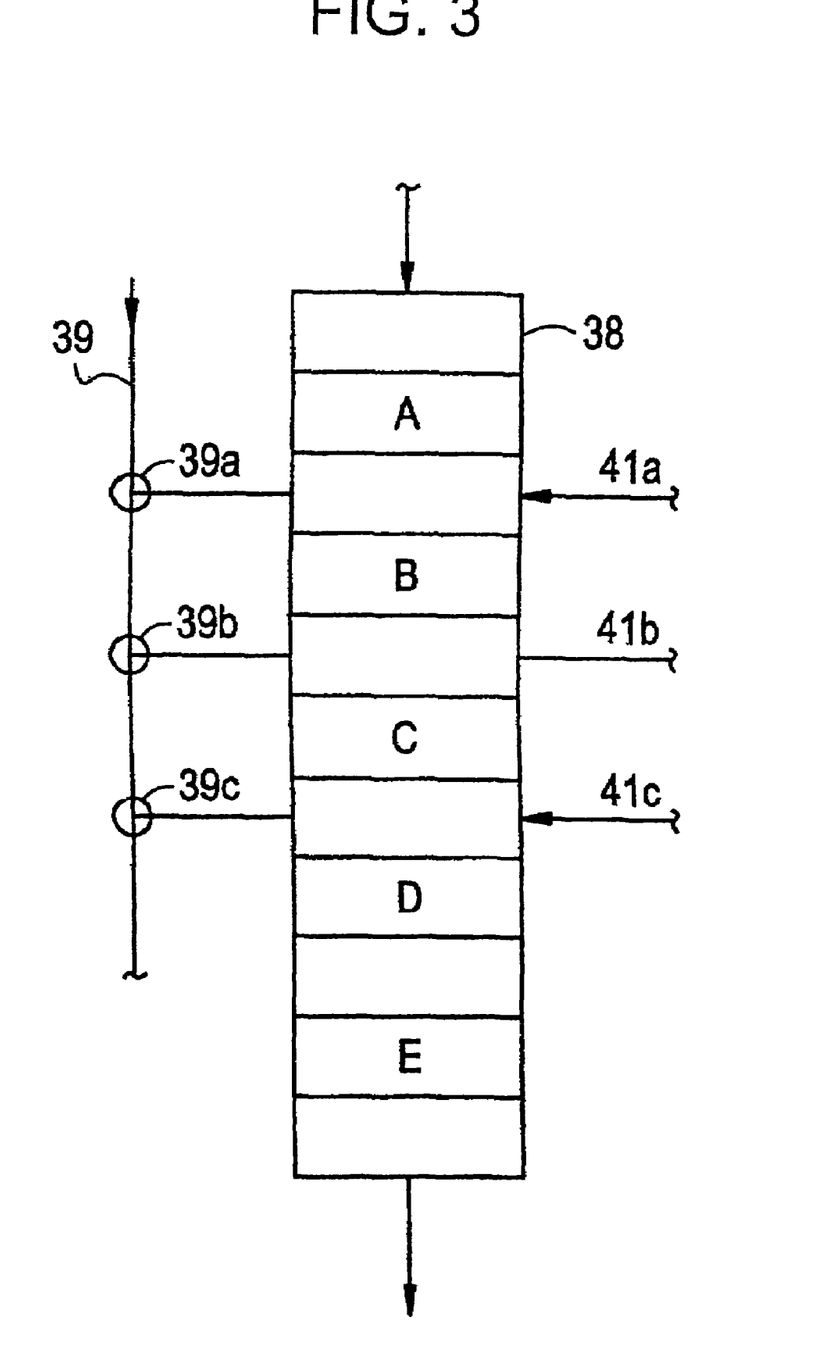
FIG. 3 is a schematic illustration of an alkylation reactor comprising a plurality of series connected catalyst beds with the interstate injection of feed components.

A preferred reactor configuration is shown in detail in FIG. 3. As illustrated there, the reactor 38 comprises five series connected catalyst beds designated as beds A, B, C, D and E. A polyethylbenzene, benzene and ethylene feed stream is supplied to the top of the reactor and into Bed A. An ethylene feed stream is supplied via line 39 and proportionating valves 39a, 39b and 39c to provide for the appropriate interstage injection of ethylene. Benzene and diethylbenzene can also be introduced between the catalyst stages by means of secondary benzene supply lines 41a, 41b and 41c, respectively. As will be recognized, the parallel reactor 38a will be configured with similar manifolding as shown in FIG. 3 with respect to reactor 38.

Returning to FIG. 2, the effluent stream from one or both of the alkylation reactors 38 and 38a is supplied through a two-way, three-position outlet valve 44 and outlet line 45 to a two-stage benzene recovery zone which comprises as the first stage a prefractionation column 47. Column 47 is operated to provide a light overhead fraction including benzene which is supplied via line 48 to the input side of heater 34 where it is mixed with benzene in line 32 and then to the alkylation/transalkylation reactor input line 30. A heavier liquid fraction containing benzene, ethylbenzene and polyethylbenzene is supplied via line 50 to the second stage 52 of the benzene separation zone. Stages 47 and 52 may take the form of distillation columns of any suitable type, typically columns having from about 20-60 trays. The overhead fraction from column 52 contains the remaining benzene which is recycled via line 54 to the alkylation reactor input. Thus, lines 48 and 54 correspond to the output line 8 of FIG. 1. The heavier bottoms fraction from column 52 is supplied via line 56 to a secondary separation zone 58 for the recovery of ethylbenzene. The overhead fraction from column 58 comprises relatively pure ethylbenzene which is supplied to storage or to any suitable product destination by way of line 60. By way of example, the ethylbenzene may be used as a feed stream to a styrene plant in which styrene is produced by the dehydrogenation of ethylbenzene. The bottoms fraction containing polyethylbenzenes, heavier aromatics such as cumene and butyl benzene, and normally only a small amount of ethylbenzene is supplied through line 61 to a tertiary polyethylbenzene separation zone 62. As described below, line 61 is provided with a proportioning valve 63 which can be used to divert a portion of the bottoms fraction for recycling back directly to the alkylation transalkylation reactor. The bottoms fraction of column 62 comprises a residue, which can be withdrawn from the process via line 64 for further use in any suitable manner. The overhead fraction from column 62 comprises a polyalkylated aromatic component containing diethylbenzene and a smaller amount of triethylbenzene and a minor amount of ethylbenzene is recycled to the alkylation/transalkylation reaction zone. By minimizing the amount of ethylbenzene recovered from the bottom of column 58, the ethylbenzene content of the polyethylbenzene stream recycled to the critical phase reactor can be kept small in order to drive the transalkylation reaction in the critical phase reactor in the direction of ethylbenzene production. The polyethylbenzene fraction withdrawn overhead from column 62 is recycled back to the alkylation/transalkylation reactor via line 66. The weight ratio of benzene to polyethylbenzene should be at least 1:1 and preferably is within the range of 1:1 to 4:1.

Returning to the operation of the separation system, in one mode of operation the entire bottoms fraction from the ethylbenzene separation column 58 is applied to the tertiary separation column 62 with overhead fractions from this zone then recycled to the alkylation/transalkylation reactor. This mode of operation offers the advantage of relatively long cycle lengths of the catalyst in the reactor between regeneration of the catalyst to increase the catalyst activity. Another mode of operation of the invention achieves this advantage by supplying a portion of the output from the ethylbenzene separation column 58 through valve 63 directly for recycle to the alkylation/transalkylation reactor.

As shown in FIG. 2, a portion of the bottoms fraction from the secondary separation zone 58 bypasses column 62 and is recycled directly to the alkylation/transalkylation reactor via valve 63 and line 88. A second portion of the bottoms fraction from the ethylbenzene column is applied to the tertiary separation column 62 through valve 63 and line 90. The overhead fraction from column 62 is withdrawn via line 66 and commingled with the bypass effluent in line 88 and the resulting mixture is fed to the alkylation transalkylation reactor via line 67. In this mode of operation a substantial amount of the bottoms product from column 58 can be recycled directly to the alkylation transalkylation reactor, bypassing the polyethylbenzene column 62. Normally, the weight ratio of the first portion recycled via line 88 directly to the alkylation transalkylation reactor to the second portion supplied initially via line 90 to the polyethylbenzene column would be within the range of about 1:2 to about 2:1. However, the relative amounts may vary more widely to be within the range of a weight ratio of the first portion to the second portion in a ratio of about 1:3 to 3:1.

The molecular sieve catalyst employed in the critical phase alkylation reactor is a zeolite beta catalyst that can be a conventional zeolite beta modified by the inclusion of cerium as described below. The cerium-promoted zeolite beta catalyst will normally be formulated in extrudate pellets of a size of about ⅛ inch or less, employing a binder such as silica or alumina. A preferred form of binder is silica, which results in catalysts having somewhat enhanced deactivation and regeneration characteristics than zeolite beta formulated with a conventional alumina binder. Typical catalyst formulations may include about 20 wt. % binder and about 80 wt. % molecular sieve.

The cerium-promoted zeolite beta employed in the critical phase alkylation transalkylation reactor can be a zeolite beta of the type described in U.S. Pat. No. 3,308,069 to Wadlinger or U.S. Pat. No. 4,642,226 to Calvert, which has been modified by the inclusion of cerium in the crystalline framework. The cerium-promoted zeolite beta employed in the present invention can be based on a high silica/alumina ratio zeolite beta or a ZSM-12 modified zeolite beta as described in U.S. Pat. No. 5,907,073 to Ghosh, the entire disclosure of which is incorporated herein by reference.

Basic procedures for the preparation of zeolite beta are well known to those skilled in the art. Such procedures are disclosed in the aforementioned U.S. Pat. No. 3,308,069 to Wadlinger et al and U.S. Pat. No. 4,642,226 to Calvert et al. and European Patent Publication No. 159,846 to Reuben, the entire disclosure of which are incorporated herein by reference. The zeolite beta can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al., zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. Unless steps are taken to minimize the alumina content, the resulting zeolite beta is normally characterized by a silica to alumina molar ratio (expressed as $SiO_2/Al_2O_3$) of between about 20 and 50.

The zeolite beta is then subjected to ion exchange with ammonium ions at uncontrolled pH. It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours.

Zeolite beta can be characterized by its crystal structure symmetry and by its x-ray diffraction patterns. Zeolite beta is a molecular sieve of medium pore size, about 5-6 angstroms, and contains 12-ring channel systems. Zeolite beta is of tetragonal symmetry $P4_122$, a=12.7, c=26.4 Å (W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The framework topology of zeolite beta," *Zeolites*, 1988, Vol. 8, November, pp. 446-452, the entire disclosure of which is incorporated herein by reference.

The cerium-promoted zeolite beta employed in carrying out the present invention may be based upon conventional zeolite beta, such as disclosed in the aforementioned patent to Calvert et al. For a further description of procedures for producing zeolite beta useful in accordance with the present invention, reference is made to the aforementioned U.S. Pat. No. 3,308,069 to Wadlinger, U.S. Pat. No. 4,642,226 to Calvert, and U.S. Pat. No. 5,907,073 to Ghosh and EPA Publication No. 507,761 to Shamshoum, the entire disclosures of which are incorporated herein by reference.

The invention can also be carried out with a zeolite beta having a higher silica/alumina ratio than that normally encountered. For example, as disclosed in EPA Publication No. 186,447 to Kennedy, a calcined zeolite beta can be dealuminated by a steaming procedure in order to enhance the silica/alumina ratio of the zeolite. Thus, as disclosed in Kennedy, a calcined zeolite beta having a silica/alumina ratio of 30:1 was subjected to steam treatment at 650° C. and 100% steam for 24 hours at atmospheric pressure. The result was a catalyst having a silica/alumina ratio of about 228:1, which was then subjected to an acid washing process to produce a zeolite beta of 250:1. Various zeolite betas, such as described above, can be subject to extraction procedures in order to extract aluminum from the zeolite beta framework by extraction with nitric acid. Acid washing of the zeolite beta is carried out initially to arrive at a high silica/alumina ratio zeolite beta. This is followed by ion-exchanging cerium into the zeolite framework. There should be no subsequent acid washing in order to avoid removing cerium from the zeolite.

The procedure disclosed in EP 507,761 to Shamshoum, et al. for incorporation of lanthanum into zeolite beta can be employed to produce the cerium-promoted zeolite beta used in the present invention. Thus cerium nitrate may be dissolved in deionized water and then added to a suspension of zeolite beta in deionized water following the protocol disclosed in EP 507,761 for the incorporation of lanthanum into zeolite beta by ion exchange. Following the ion exchange procedure, the cerium exchanged zeolite beta can then be filtered from solution washed with deionized water and then dried at a temperature of 110° C. The powdered cerium exchanged zeolite beta can then be molded with an aluminum or silicon binding agent followed by extrusion into pellet form.

In experimental work carried out respecting the present invention alkylation/transalkylation was carried out employing a single stage alkylation reactor. The reactor operated as a laboratory simulation of the single stage of a multiple stage reactor of the type illustrated in FIG. 3. In carrying out the experimental work, a cerium-promoted zeolite beta having a silica alumina ratio of 150 and a cerium/aluminum atomic ratio of 0.75 was employed. This catalyst was formed employing a silica binder.

The single stage reactor was operated at a temperature within the range of 315-325° C. and at a pressure of about 750 psia. Benzene was supplied to the top of the reactor and a product stream including unreacted benzene, ethylbenzene and polyethylbenzene were recovered from the bottom of the reactor. The product recovered from the reactor was split into two fractions, one fraction being employed in an internal recycle to the reactor and the other fraction subjected to downstream separation procedures to recover benzene, ethylbenzene, polyethylbenzene and a heavy residue component, which was withdrawn from the process. The weight ratio of product fraction of ethylbenzene and polyethylbenzenes recycled to the reactor in the internal recycle to the fraction passed to the separation system was within the range of 3:1 to 6:1. The separation system was operated to separate ethyl benzene, which was withdrawn from the process, benzene and polyethylbenzene, which were recycled to the inlet side of the reactor. Fresh benzene and ethylene were, of course, supplied to the top of the reactor. In operation of the experimental reactor, the polyethylbenzene produced was monitored, and with continued operation, approached an equilibrium condition in which no additional polyethylbenzene was produced. Since polyethylbenzene as well as ethylbenzene was continually produced by the alkylation reactor with only ethylbenzene being withdrawn from the system, the equilibration condition reached by the polyethylbenzene content confirmed that some of the polyethylbenzene was being eliminated by the system by a transalkylation reaction carried on concurrently with the alkylation reaction.

Figure 4:
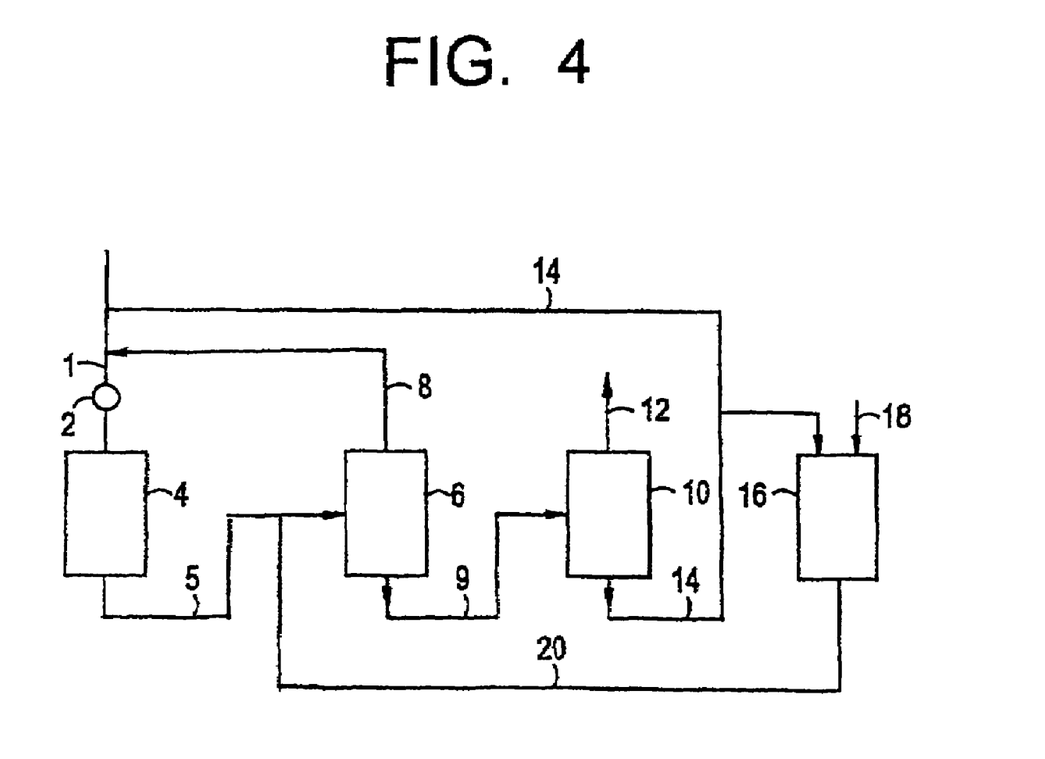
FIG. 4 is a schematic block diagram of another embodiment of the invention.

While the present invention can be carried out with transalkylation occurring only in the alkylation/transalkylation reactor, in a further embodiment of the invention, a separate transalkylation reactor can be employed to provide a secondary transalkylation function. A schematic illustration of this embodiment of the invention is illustrated in FIG. 4. In FIG. 4, like components as shown in FIG. 1 are indicated by the same reference numerals as employed in FIG. 1. In operation of the system shown in FIG. 4, a first portion of the polyethylbenzene fraction is supplied via line 14 for recycle to reactor 4 as described previously. A second portion is split off from the recycle line and applied via line 15 to a secondary transalkylation reactor 16. Benzene is also supplied to the transalkylation reactor through line 18. The transalkylation reactor, which normally will be operated under liquid phase conditions, contains a molecular sieve catalyst, preferably zeolite Y, which has a somewhat larger pore size than the cerium-modified zeolite beta used in the initial alkylation/transalkylation reaction zone. The output from the transalkylation reactor 16, which contains the ethylbenzene product as well as some unreacted benzene and polyethylbenzene, is recycled via line 20 to the downstream separation system 6.

Having described specific embodiments of the present invention, it will be understood that modifications thereof may be suggested to those skilled in the art, and it is intended to cover all such modifications as fall within the scope of the appended claims.

The invention claimed is:

1. A process for the production of ethylbenzene comprising:
   (a) supplying an aromatic feedstock containing benzene into a reaction zone and into contact with a cerium-promoted zeolite beta molecular sieve alkylation catalyst in said reaction zone and containing cerium in an amount to provide a cerium/aluminum atomic ratio within the range of 0.25-5.0;
   (b) supplying a polyethylbenzene co-feed to said reaction zone;
   (c) supplying ethylene to said reaction zone;
   (d) operating said reaction zone at temperature and pressure conditions in which benzene is in the supercritical phase to cause ethylation of benzene and the transalkylation of polyethylbenzene and benzene in the presence of said zeolite beta alkylation catalyst to produce an alkylation product containing ethylbenzene as a primary product with the attendant production of heavier alkylated byproducts in a minor amount; and
   (e) recovering said alkylation product from said reaction zone.

2. The process of claim 1 wherein ethylene is supplied to said reaction zone in an amount to provide a benzene/ethylene mole ratio within the range of 1-15.

3. The process of claim 2 wherein the benzene to ethylene mole ratio is less than 10.

4. The process of claim 2 wherein the benzene to ethylene mole ratio is within the range of 2-5.

5. The method of claim 1 wherein said zeolite beta has a silica/alumina mole ratio within the range of 50-150.

6. The process of claim 1 wherein said zeolite beta has a cerium/aluminum atomic ratio within the range of 0.5-1.5.

7. The process of claim 1 wherein said reaction zone is operated at temperature and pressure conditions in which ethylbenzene is in the liquid phase.

8. The method of claim 1 wherein said alkylation reaction zone is operated at temperature and pressure conditions to provide a composite byproduct yield of propylbenzene and butylbenzene which is less than the corresponding composite byproduct yield of propylbenzene and butylbenzene for a zeolite beta promoted with lanthanum at a lanthanum/aluminum atomic ratio at least equal to the cerium/aluminum atomic ratio of said cerium-promoted zeolite beta catalyst under the same temperature and pressure conditions.

9. The method of claim 1 wherein said alkylation reaction zone is operated at temperature and pressure conditions to provide a composite byproduct yield of propyl benzene and butyl benzene which is no more than one half of the corresponding byproduct yield of propyl benzene and butyl benzene for a zeolite beta catalyst promoted with lanthanum at a lanthanum/aluminum atomic ratio at least equal to the cerium/aluminum atomic ratio of said catalyst under the same temperature and pressure conditions.

10. A process for the production of ethylbenzene comprising:
(a) providing an alkylation transalkylation reaction zone containing a cerium-promoted zeolite beta aromatic alkylation catalyst;
(b) supplying a feedstock containing benzene, polyethylbenzene and ethylene to said alkylation transalkylation reaction zone;
(c) operating said alkylation transalkylation reaction zone at temperature and pressure conditions in which benzene is in the supercritical phase to cause the ethylation of benzene and the transalkylation of benzene and polyethylbenzene in the presence of said cerium-promoted zeolite beta alkylation catalyst to produce a reaction product comprising a mixture of benzene, ethylbenzene and polyethylbenzene;
(d) recovering the reacted product from said alkylation transalkylation reaction zone and supplying said product from said alkylation transalkylation reaction zone to a recovery zone for the separation and recovery of ethylbenzene from the alkylated product and the separation and recovery of a polyalkylated aromatic component including diethylbenzene;
(e) recycling at least a portion of the polyalkylated aromatic component including diethylbenzene in said polyalkylated aromatic component to said alkylation/transalkylation reaction zone; and
(f) continuing the supply of benzene to said alkylation/transalkylation reaction zone to cause disproportionation of said polyalkylated aromatic fraction to produce a disproportionation product having a reduced diethylbenzene content and an enhanced ethylbenzene content.

11. The process of claim 10 wherein said cerium-promoted zeolite beta alkylation catalyst has a silica/alumina mole ratio within the range of 50-150.

12. The process of claim 11 herein said catalyst has a cerium/aluminum atomic ratio within the range of 0.25-1.25.

13. The method of claim 10 wherein said cerium-promoted zeolite beta is formed with a silica binder.

14. The method of claim 10 wherein said alkylation zone is operated at temperature and pressure conditions to provide a composite byproduct yield of propylbenzene and butylbenzene which is less than the corresponding composite byproduct yield of propylbenzene and butylbenzene for a zeolite beta promoted with lanthanum at a lanthanum/aluminum atomic ratio at least equal to the cerium/aluminum atomic ratio of said cerium-promoted zeolite beta catalyst under the same temperature and pressure conditions.

15. The process of claim 10 wherein a predominant portion of the polyalkylated aromatic component is recycled to said alkylation/transalkylation reaction zone.

16. The process of claim 10 wherein substantially all of the polyalkylated aromatic component is recycled to said alkylation/transalkylation reaction zone.

17. The process of claim 10 wherein a second portion of the polyalkylated aromatic component recovered from said recovery zone is supplied to a separate secondary transalkylation reactor.

18. The process of claim 17 wherein said secondary transalkylation reactor is operated under liquid phase conditions and contains a zeolite molecular sieve catalyst having a larger pore size than the pore size of the cerium-modified zeolite beta in said alkylation/transalkylation reaction zone.

19. The process of claim 18 wherein said molecular sieve catalyst in said secondary transalkylation zone is zeolite Y.

20. The process of claim 10 wherein said alkylation/transalkylation reaction zone is operated at temperature and pressure conditions at which ethyl benzene is in the liquid phase.

* * * * *